US00PP18735P2

(12) United States Plant Patent
Takeshita

(10) Patent No.: US PP18,735 P2
(45) Date of Patent: Apr. 15, 2008

(54) ***LOBELIA* PLANT NAMED 'KIRILO-LV63'**

(50) Latin Name: ***Lobelia richardsoni*×*Lobelia Erinus***
Varietal Denomination: Kirilo-LV63

(75) Inventor: Daigaku Takeshita, Tochigi-ken (JP)

(73) Assignee: Kirin Brewery Co. Ltd., Tokyo (JP)

( * ) Notice: Subject to any disclaimer, the term of this patent is extended or adjusted under 35 U.S.C. 154(b) by 67 days.

(21) Appl. No.: 11/489,196

(22) Filed: Jul. 19, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Lobelia* plant named 'Kirilo-LV63', characterized by its low mounding, outwardly spreading to cascading plant habit; freely branching habit; dense and bushy plant form; continuously and freely flowering habit; dark blue-colored flowers; relatively tolerant to high temperatures; and good garden performance.

1 Drawing Sheet

Botanical designation: *Lobelia richardsoni*×*Lobelia erinus.*
Cultivar denomination: 'Kirilo-LV63'.

BACKGROUND OF THE INVENTION

The present invention relates to a new and distinct cultivar of *Lobelia,* botanically known as *Lobelia richardsonii*× *Lobelia erinus* and hereinafter referred to by the name 'Kirilo-LV63'.

The new *Lobelia* is a product of a planned breeding program conducted by the Inventor in Tochigi, Japan. The objective of the breeding program is to create new *Lobelia* cultivars with good vigor and high temperature tolerance.

The new *Lobelia* originated from a cross-pollination made by the Inventor in March, 2003 of an unnamed selection of *Lobelia richardsonii,* not patented, as the female, or seed, parent with an unnamed selection of *Lobelia erinus,* not patented, as the male, or pollen, parent. The new *Lobelia* was discovered and selected by the Inventor as a single flowering plant with the progeny of the stated cross-pollination grown in a controlled environment in Tochigi, Japan in October, 2003.

Asexual reproduction of the new cultivar by terminal cuttings in Tochigi, Japan, has shown that the unique features of this new *Lobelia* are stable and reproduced true to type in successive generations.

SUMMARY OF THE INVENTION

Plants of the cultivar Kirilo-LV63 have not been observed under all possible environmental conditions. The phenotype may vary somewhat with variations in environment such as temperature and light intensity without, however, any variance in genotype.

The following traits have been repeatedly observed and are determined to be the unique characteristics of 'Kirilo-LV63'. These characteristics in combination distinguish 'Kirilo-LV63' as a new and distinct cultivar of *Lobelia:*

1. Low mounding, outwardly spreading to cascading plant habit.
2. Freely branching habit; dense and bushy plant form.
3. Continuously and freely flowering habit.

4. Dark blue-colored flowers.
5. Relatively tolerant to high temperatures.
6. Good garden performance.

Plants of the new *Lobelia* differ from plants of the female parent selection in the following characteristics:

1. Plants of the new *Lobelia* are more vigorous than plants of the female parent selection.
2. Plants of the new *Lobelia* are more mounding than plants of the female parent selection.
3. Plants of the new *Lobelia* flower more freely and earlier than plants of the female parent selection.
4. Plants of the new *Lobelia* had darker blue-colored flowers than plants of the female parent selection.

Plants of the new *Lobelia* differ from plants of the male parent selection in the following characteristics:

1. Plants of the new *Lobelia* are larger and more mounding than plants of the male parent selection.
2. Plants of the new *Lobelia* have thinner stems than plants of the male parent selection.
3. Flowers of plants of the new *Lobelia* are not fragrant whereas flowers of plants of the male parent selection are fragrant.

Plants of the new *Lobelia* can be compared to plants of the cultivar Loboudtis, disclosed in U.S. Plant Pat. No. 15,526. In side-by-side comparisons conducted by the Inventor in Tochigi, Japan, plants of the new *Lobelia* differed from plants of the cultivar Loboudtis in the following characteristics:

1. Plants of the new *Lobelia* were larger than plants of the cultivar Loboudtis.
2. Plants of the new *Lobelia* flowered later than plants of the cultivar Loboudtis.
3. Plants of the new *Lobelia* were more high temperature tolerant than plants of the cultivar Loboudtis.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the actual colors of the new *Lobelia*. The photograph comprises a side perspective view of a typical flowering plant of 'Kirilo-LV63' grown in a container.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photograph and following description were grown under conditions which closely approximate commercial production conditions during the late spring in a polyethylene-covered greenhouse in Santa Paula, Calif. for about 10 to 13 weeks in 15-cm containers. During the production of the plants, day temperatures ranged from 16° to 27° C., night temperatures ranged from 7° to 15° C. and light levels ranged from 5,000 to 7,000 foot-candles. Plants were pinched one time about four weeks after planting.

Botanical classification: *Lobelia richardsonii*×*Lobelia erinus* cultivar Kirilo-LV63.

Parentage:

*Female parent.*—Unnamed selection of *Lobelia richardsonii,* not patented.

*Male parent.*—Unnamed selection of *Lobelia erinus,* not patented.

Propagation:

*Type cutting.*—Terminal vegetative cuttings.

*Time to initiate roots, summer.*—About three days at 23° C.

*Time to initiate roots, winter.*—About five days at 20° C.

*Time to produce a rooted young plant, summer.*—About 21 days at 23° C.

*Time to produce a rooted young plant, winter.*—About 23 days at 20° C.

*Root description.*—Fine, fibrous; white in color.

*Rooting habit.*—Freely branching; moderately dense.

Plant description:

*Form.*—Low mounding, outwardly spreading to cascading plant habit. Freely branching, about twelve main stems each with numerous secondary lateral branches; dense and bushy plant habit; moderately vigorous growth habit.

*Plant height.*—About 18 cm.

*Plant width.*—About 65 cm.

*Lateral branch description.*—Length: About 34 cm. Diameter: About 3.5 mm. Internode length: About 1.75 cm. Strength: Strong. Aspect: Mostly outwardly spreading, curling upwards towards the apex. Texture: Smooth, glabrous. Color: 147A.

Foliage description:

*Arrangement.*—Alternate, simple.

*Length, basal leaves.*—About 5 cm.

*Length, apical leaves.*—About 4.2 cm.

*Width, basal leaves.*—About 2.2 cm.

*Width, apical leaves.*—About 1.5 cm.

*Shape.*—Elliptical.

*Apex.*—Acute.

*Base.*—Attenuate.

*Margin.*—Serrate.

*Texture, upper and lower surfaces.*—Smooth, glabrous.

*Venation pattern.*—Pinnate; arcuate.

*Color.*—Developing and fully expanded foliage, upper surface: 147A; venation, 147B. Developing and fully expanded foliage, lower surface: 147B; venation, 147B.

*Petiole length.*—About 5 mm.

*Petiole diameter.*—About 4 mm.

*Petiole texture.*—Smooth, glabrous.

*Petiole color.*—147B.

Flower description:

*Flower arrangement/shape.*—Flowers arranged singly at lateral apices. Flowers held mostly outwardly. Flowers persistent. Flowering continuous; older flowers are overgrown by new flowers and foliage. Freely flowering habit, about 35 flowers per lateral stem. Flowers not fragrant. Flowers tubular with three larger lower petals and two upright petals.

*Natural flowering season.*—Spring until frost in the autumn.

*Flower longevity on the plant.*—Longevity of individual flowers is highly dependent on weather conditions; typically about one week.

*Flower size.*—Diameter: About 1.7 cm by 1.7 cm. Depth (height): About 2 cm.

*Flower buds.*—Length: About 1.8 cm. Diameter: About 4 mm. Shape: Obovate. Color: 97D.

*Petals.*—Arrangement: Single whorl of five petals, fused; three larger lower petals and two smaller upper petals. Three lower petals: Shape: Rounded. Length, above throat: About 1 cm. Width: About 6 mm. Two upper petals: Shape: Elliptical. Length, above throat: About 8 mm. Width: About 2.5 mm. Upper and lower petals: Apex: Rounded to acuminate. Margin: Entire. Texture, upper and lower surfaces: Smooth, satiny. Color: When opening, upper and lower surfaces: 97C to 97D. Fully opened, upper surface: 94A; towards base of lower petals, irregular white patch, 155D, with small dot, 93B. Fully opened, lower surface: 94C to 94D.

*Sepals.*—Arrangement: Single whorl of five sepals, fused at the base; star-shaped calyx. Length: About 1 cm. Width: About 1 mm. Shape: Linear. Apex: Acuminate. Margin: Entire. Texture, upper and lower surfaces: Smooth, glabrous. Color, upper and lower surfaces: 147A.

*Peduncles.*—Length: About 2.75 cm. Diameter: About 1 mm. Angle: About 45° from the stem axis. Texture: Smooth, glabrous. Color: 147A.

*Reproductive organs.*—Stamens: Quantity per flower: About five. Anther length: About 2 mm. Anther color: 201A. Pollen amount: Scarce. Pollen color: 94D. Pistils: Quantity per flower: One. Pistil length: About 1.5 cm. Stigma shape: Two-parted, round. Stigma color: 90B. Style length: About 1.3 cm. Style color: 145B. Ovary color: 146B.

*Seed/fruit.*—Seed and fruit production has not been observed.

Disease/pest resistance: Plants of the new *Lobelia* have not been noted to be resistant to pathogens and pests common to *Lobelia*.

Garden performance: Plants of the new *Lobelia* have exhibited good tolerance to rain and wind and have been observed to tolerate temperatures from about 4° C. to about 28° C.

It is claimed:

1. A new and distinct *Lobelia* plant named 'Kirilo-LV63' as illustrated and described.

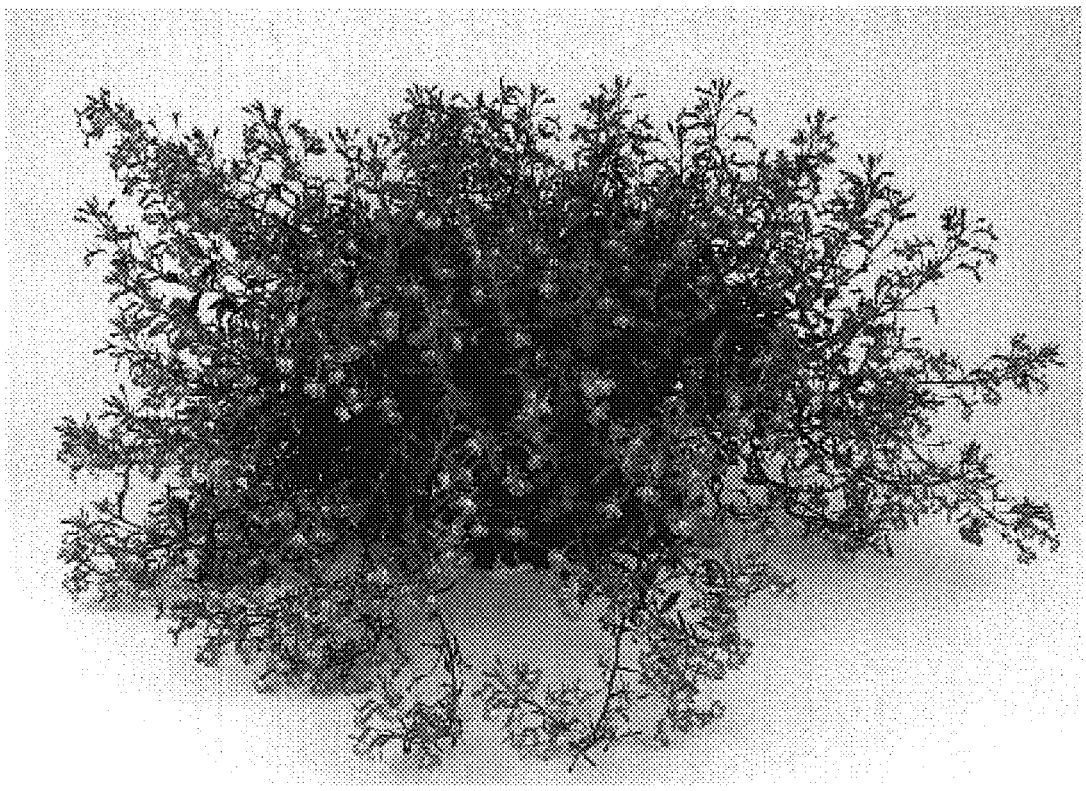

* * * * *